United States Patent
Grusin et al.

(10) Patent No.: US 6,554,865 B2
(45) Date of Patent: Apr. 29, 2003

(54) HUMERAL STEM WITH DISTAL TRI-SLOT

(75) Inventors: N. Kelley Grusin, Memphis, TN (US); Lance Wolf, New Albany, IN (US); Lauralan Terrill-Grisoni, Cordova, TN (US); Christopher Jobe, Redland, CA (US); Charles Sorbie, Kingston (CA); William J. Mallon, Arlington, TN (US); Stuart Patterson, Winter Haven, FL (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 09/838,736

(22) Filed: Apr. 19, 2001

(65) Prior Publication Data

US 2002/0183849 A1 Dec. 5, 2002

(51) Int. Cl.[7] ............... A61F 2/40; A61F 2/32; A61F 2/36; A61F 2/38
(52) U.S. Cl. ............ 623/19.14; 623/22.4; 623/22.41; 623/23.15; 623/20.36; 623/23.19
(58) Field of Search ............ 623/19.14, 19.13, 623/23.15, 23.26, 23.31, 23.32–23.35, 23.11, 23.18, 23.19, 23.44, 22.4, 22.42, 22.41

(56) References Cited

U.S. PATENT DOCUMENTS

| | | | | |
|---|---|---|---|---|
| 5,002,578 A | * | 3/1991 | Luman | 623/23 |
| 5,152,799 A | | 10/1992 | Lyons | 623/23 |
| 5,653,765 A | * | 8/1997 | McTighe et al. | 623/23 |
| 5,702,482 A | * | 12/1997 | Thongpreda et al. | 623/23 |
| 5,735,898 A | * | 4/1998 | Branemark | 623/16 |
| 6,200,349 B1 | * | 3/2001 | Naybour | 623/23.15 |

FOREIGN PATENT DOCUMENTS

| | | | |
|---|---|---|---|
| DE | 34 26 947 A1 | 7/1984 | A61F/2/36 |
| DE | 43 32 230 A1 | 9/1993 | A61F/2/36 |
| DE | 195 15 310 A1 | 4/1995 | A61F/2/36 |
| EP | 0 452 253 A1 | 3/1991 | A61F/2/36 |
| EP | 0 480 872 A1 | 9/1991 | A61F/2/36 |
| EP | 0 543 099 A2 | 9/1992 | A61F/2/36 |
| EP | 0 668 064 A1 | 2/1994 | A61F/2/36 |
| EP | 0 765 644 A2 | 9/1996 | A61F/2/28 |
| EP | 0 815 809 A2 | 6/1997 | A61F/2/30 |
| EP | 0 970 666 A2 | 7/1999 | A61F/2/36 |
| FR | 2 549 717 A1 | 7/1983 | A61F/2/32 |
| SU | 1526684 | * 12/1989 | 623/19 |
| WO | WO 95/22302 | 8/1995 | A61F/2/36 |

* cited by examiner

Primary Examiner—Corrine McDermott
Assistant Examiner—Alvin Stewart
(74) Attorney, Agent, or Firm—Fredrikson & Byron, P.A.

(57) ABSTRACT

A series of humeral stems, each stem including an axial bore and longitudinal slots along the distal end to allow for distal compression. The compression force necessary to compress the distal diameter of each stem varies by stem diameter. Thus, as the stem diameter increases through the series, the compression force decreases.

4 Claims, 1 Drawing Sheet

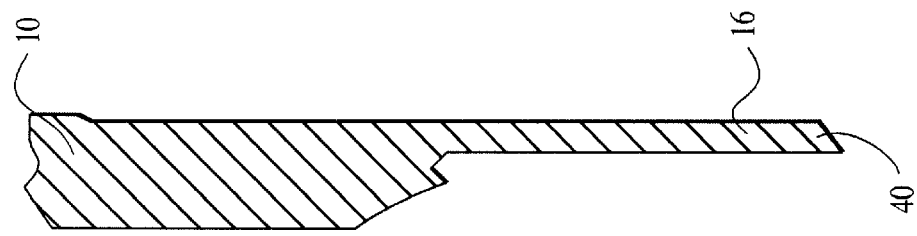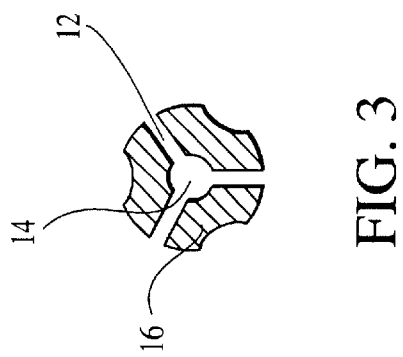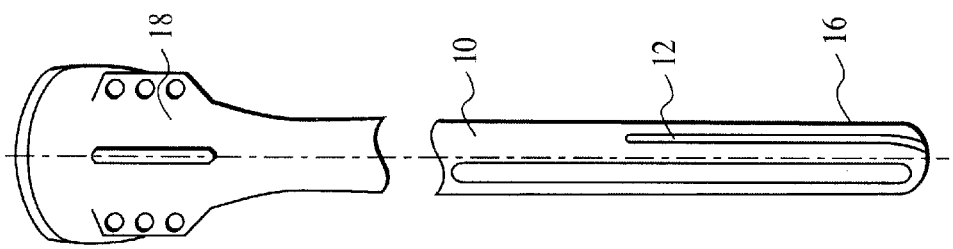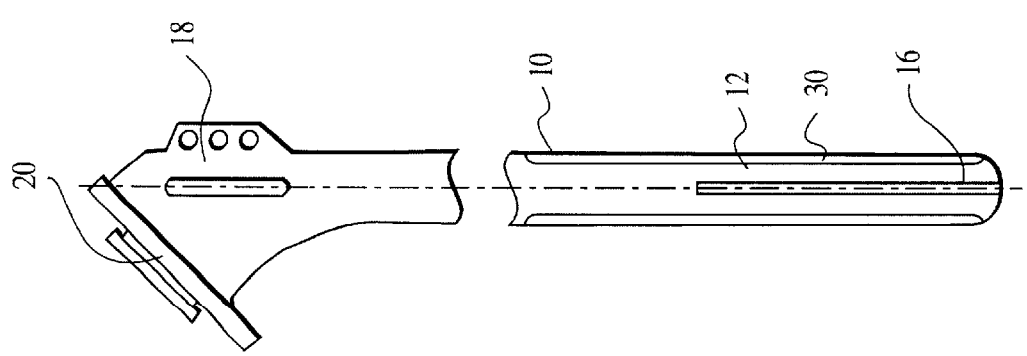

HUMERAL STEM WITH DISTAL TRI-SLOT

FIELD OF THE INVENTION

The present invention relates to a humeral prosthesis. More particularly, the present invention relates to a series of humeral stems, each stem head having an axial bore and longitudinal slots along the distal end to allow for distal compression. The compression force necessary to compress the distal diameter of the stem varies by stem diameter. Thus, as the stem diameter increases, the compression force decreases, thereby relieving cortical wall pressure in potentially thinner cortical walls.

BACKGROUND OF THE INVENTION

Shoulder replacement operations involve replacing at least a portion of the proximal section of the humeral shaft with a prosthesis. Typically, the medullary canal of the humerus is reamed or bored at its upper end for receiving the prosthesis. A stem portion of the prosthesis is inserted into the reamed portion of the humerus in a secure position. The stem engages an artificial humeral head for receipt by the glenoid cavity.

Early shoulder prostheses were typically unitary structures including a stem, to be implanted within the humerus, and a head, to be positioned within the glenoid cavity of the scapula, attempting to directly mimic the unitary structure of the upper portion of the humerus that they were designed to replace.

Due to several problems with the a conventional unitary shoulder prosthesis, among them the necessity of maintaining a large inventory of differently configured prostheses in order to accommodate the varying morphologies of patients, assorted modular prostheses have been developed. A modular prosthesis generally consists of two parts: a stem that is mounted into the medullary canal of the humerus, and a head component connected in some manner to the stem. The head component replaces the bearing surface of the scapula to allow the movement of the shoulder. Different stem sizes and head sizes in a modular prosthesis provide the surgeon with some degree of inter-operative flexibility which facilitates reconstruction of the original anatomy of the patient. With a range of stem sizes and a range of head sizes available, the surgeon can choose a particular combination to suit the anatomy of each individual without having to have a large inventory of unitary humeral prostheses.

While modular prostheses have solved a number of problems prevalent in the prior art, others remain. For example, unitary as well as modular prostheses typically fail to maximize flexibility of the stem portion in order to reduce hoop stress during insertion of the stem.

SUMMARY OF THE INVENTION

The present invention relates generally to shoulder prostheses. In particular, the invention provides a series of humeral stems having increased stability and distal flexibility to relieve humeral pain. Generally, the stems are for use in a modular shoulder prosthesis. However, if desired, a unitary prosthesis could be designed having a stem configured as taught herein. The stem has utility in any prosthesis in which a stem of the prosthesis is to be inserted into the intermedullary canal of the bone, such as a shoulder, hip, knee, or finger prosthesis.

The modular humeral prosthesis generally comprises a stem to be fitted to a resected humerus and a head sized and configured to approximate the humeral head. Optionally, one or more connecting members may be used to connect the stem to the head in a variety of configurations. For example, the connecting member could be used to achieve varying degrees of eccentricity (offset) or tilt of the head to the stem. The humeral head has a spherical surface on one side and a flat face on the opposite side. The spherical surface replaces the bearing surface of the normal humeral head to allow movement of the shoulder Each stem of the series is shaped for insertion into the reamed portion of the medullary canal of the humerus. Each stem includes an axial bore and a series of longitudinal slots are spaced around the distal portion of the stem allow for distal compression. The size and length of the bore as well as the length of the slots are codependent and determine the compression force necessary to compress the distal diameter of the stems by a predetermined amount. The bore and slots are sized and configured such that the compression force needed to compress each stem decreases as the diameter of the stem increases. Preferably, a series of stems is provided having varying diameters.

Thus, the stem reduces hoop stress during insertion of the stem. The stem is especially effective in relieving cortical wall pressures in potentially thinner cortical walls.

BRIEF DESCRIPTION OF THE DRAWINGS

FIG. 1 a side view of one embodiment of the present invention;

FIG. 2 is a rear virew of one embodiment of the present invention;

FIG. 3 is a cross-sectional view of the distal end of one embodiment of the invention;

FIG. 4 is a cross-sectional view of one embodiment of the invention.

DETAILED DESCRIPTION OF THE PREFERRED EMBODIMENTS

In the drawings, like structures are provided with like reference numerals.

FIG. 1 illustrates a side view of a first embodiment of the present invention. Stem 10 generally comprises proximal portion 18 and distal portion 10. Proximal portion 18 has engagement structure 20 provided thereon for engaging a functional element, for example a joint structure. An axial bore 14 (FIG. 3) extends through distal portion 10. Slots 12 are provided along distal portion 10. Preferably, three or more slots are provided, and are equiangularly arranged about the circumference of the stem. While three stem segments is preferred, any number of stem segments (above three) may be provided. Note, however, that there is a possibility of lateral slippage if an even number of stem segments are provided. Thus, it is recommended that an odd number of stem segments be provided. It is desirable that the stem be manufactured of titanium 6-4. However, any suitable bio-compatible material may be used to manufacture the stem.

The axial bore and slots 12 define a plurality of elongated, axially extending stem segments 16. Stem segments 16 are capable of being radially compressed upon insertion into the intermedullary canal of a bone. The bore and slots 12 are sized and configured for differently sized stems in a series of stems such that as the stem diameter increases, the compressive force needed to compress the distal portion of the stem decreases. Grooves 30 are provided along stem segments 16 to for receiving cement to fixate stem in medullary canal. Preferably, the bores and slots are sized to enable a movement of at least 1 mm for each stem segment at its distal end. The length and diameter of the axial bore are cooperatively adjusted to dictate the compressive force required.

As one example, the length and diameter of the axial bore of a series of stems may be such as to provide the following values for 1 mm distal compression:

| DISTAL STEM DIAMETER (MM) | COMPRESSION FORCE (LBS) |
|---|---|
| 10 | 20 |
| 12 | 16 |
| 14 | 12 |
| 16 | 10 |

A finite element analysis may be performed by bringing the stem segments towards the center of the axial bore until they contact one another, and measuring the compression force used in order to determine optimal configurations. Alternatively, a pressure gage may be inserted into the bore to measure the pressure applied, or a force gage may be used to indicate the radial force applied.

FIG. 2 shows a rear view of one embodiment of the stem of the present invention. The stem is of approximately equal diameter along distal portion 10, widening at the upper section of proximal portion 18. The axial bore and slots 12 are provided along a length of distal portion 10 sufficient to allow for a desired amount of compression upon application of a compressive force, the diameter of the stem being measured along the stem length having the slots.

As seen in FIG. 3, showing a cross-sectional view of the distal end of the stem, axial bore 14 and slots 12 define a plurality of elongated, axially extending stem segments 16. The size and configuration of bore 14 and slots 12 determine the compressive force necessary to compress the distal portion of the stem. Compressive force applied to the stem, by insertion of the stem into the intermedullary canal of a bone, for example, causes stem segments 16 to be radially compressed. Grooves 30 are provided along stem segments 16 to for receiving cement to fixate stem in medullary canal.

FIG. 4 depicts a cross-sectional view of a stem segment. Stem segment 16 extends along the longitudinal axis of distal portion 10 of the stem framing the axial bore. Stem segment 16 is rounded distally at end 40 to allow for smooth insertion into the intermedullary canal.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A series of sized stems for insertion in the intermedullary canal of a bone, each stem comprising:

a proximal end portion having an engagement structure provided thereon; and a distal end portion having an axial bore and an odd number of slots extending proximally therefrom, at least three slots being provided, and defining a plurality of elongated, axially extending stem segments;

each stem of the series having a diameter, the diameter of the stems varying between stems;

each stem segment being capable of radial compression upon application of a compression force, the bore and slots of the series being sized and configured such that the compressive force needed to compress each of the segments decreases as the diameter of the stems increase.

2. The series of claim 1, wherein the stems are manufactured of titanium.

3. The series of claim 1, further comprising a groove provided along each stem segment for receiving adhesive.

4. A series of sized prostheses, each having a stem for insertion in the intermedullary canal of a bone, each stem comprising:

a proximal end portion;

a functional element carried on the proximal end portion;

a distal end portion having an axial bore and three or more slots extending proximally therefrom and defining a plurality of elongated, axially extending stem segments;

each stem of the series having a diameter, the diameter of the stems varying between stems;

each stem segment being capable of radial compression upon application of a compression force, the bore and slots of the series being sized and configured such that the compressive force needed to compress each of the segments decreases as the diameter of the stems increase.

* * * * *